United States Patent [19]

Zocchi

[11] Patent Number: 5,683,972
[45] Date of Patent: *Nov. 4, 1997

[54] FOAMING OIL-IN-WATER EMULSION

[75] Inventor: Germaine Zocchi, Villers-Aux-Tours, Belgium

[73] Assignee: Colgate-Palmolive Company, New York, N.Y.

[*] Notice: The term of this patent shall not extend beyond the expiration date of Pat. No. 5,518,647.

[21] Appl. No.: 622,077

[22] Filed: Mar. 26, 1996

Related U.S. Application Data

[63] Continuation of Ser. No. 170,575, Dec. 20, 1993, Pat. No. 5,518,647.

[51] Int. Cl.$^6$ .............. C11D 1/14; C11D 1/86; C11D 3/22; C11D 3/20

[52] U.S. Cl. .......... 510/135; 510/417; 510/422; 510/423; 510/424; 510/425; 510/427; 510/428; 510/433; 510/434; 510/437; 510/421; 510/426; 510/470; 510/471; 510/472; 510/473; 510/475; 510/476; 510/477; 510/497; 510/158; 510/159

[58] Field of Search .................... 252/352, 353, 252/354, 355, 356, 357, 153, 173, DIG. 1, DIG. 2, DIG. 4, DIG. 5, DIG. 7, DIG. 14, 174.15, 174.17, 547, 548, 559, 551, 174.23, 174.24, 552, 174.18, 166, 167, 170, 171, 557; 510/417, 135, 422, 423, 427, 428, 437, 421, 471, 472, 476, 477, 424, 425, 433, 434, 426, 470, 473, 475, 497, 158, 159

[56] References Cited

U.S. PATENT DOCUMENTS

| | | | |
|---|---|---|---|
| 3,988,255 | 10/1976 | Seiden | 252/DIG. 5 |
| 4,026,825 | 5/1977 | Steen et al. | 252/DIG. 14 |
| 4,554,098 | 11/1985 | Klisch et al. | 252/DIG. 14 |
| 4,657,999 | 4/1987 | Hoefer et al. | 526/200 |
| 4,839,098 | 6/1989 | Wisotzki et al. | 252/DIG. 14 |
| 4,844,756 | 7/1989 | Forsberg | 252/356 X |
| 4,948,576 | 8/1990 | Verdicchio et al. | 424/70 X |
| 5,013,473 | 5/1991 | Norbury et al. | 252/DIG. 5 |
| 5,019,376 | 5/1991 | Uick | 252/547 X |
| 5,034,218 | 7/1991 | Duvel | 252/DIG. 2 |
| 5,047,177 | 9/1991 | Varco | 252/DIG. 5 |
| 5,114,706 | 5/1992 | Duvel | 252/DIG. 2 |
| 5,133,897 | 7/1992 | Balzer | 252/356 X |
| 5,158,710 | 10/1992 | VanEenam | 252/DIG. 14 |
| 5,192,462 | 3/1993 | Gloor et al. | 252/DIG. 14 |
| 5,234,619 | 8/1993 | Greene et al. | 252/DIG. 14 |
| 5,236,612 | 8/1993 | Rahman et al. | 252/89.1 |
| 5,290,482 | 3/1994 | Marschner et al. | 252/DIG. 5 |
| 5,306,489 | 4/1994 | Goldberg et al. | 424/71 |
| 5,308,526 | 5/1994 | Dias et al. | 252/DIG. 14 |
| 5,403,517 | 4/1995 | Horinishi et al. | 252/551 |
| 5,409,628 | 4/1995 | Heinz et al. | 252/DIG. 14 |
| 5,409,640 | 4/1995 | Giret et al. | 252/DIG. 7 |
| 5,449,763 | 9/1995 | Wulff et al. | 252/DIG. 14 |
| 5,518,647 | 5/1996 | Zocchi | 510/159 |
| 5,560,872 | 10/1996 | Rahman et al. | 510/392 |

FOREIGN PATENT DOCUMENTS

| | | |
|---|---|---|
| 60372 | 9/1982 | European Pat. Off. . |
| 341071 | 11/1989 | European Pat. Off. . |
| 407042 | 1/1991 | European Pat. Off. . |
| 413417 | 2/1991 | European Pat. Off. . |
| 531650 | 3/1993 | European Pat. Off. . |
| 542526 | 5/1993 | European Pat. Off. . |
| 4129986 | 3/1993 | Germany . |
| 91/17237 | 11/1991 | WIPO . |
| 91/18963 | 12/1991 | WIPO . |
| 92/06669 | 4/1992 | WIPO . |
| 93/09761 | 5/1993 | WIPO . |
| 93/19149 | 9/1993 | WIPO . |

OTHER PUBLICATIONS

Proserpio, G., et al., "Surfactant–Cosmetic Applications of a New Gluocoside", Monthly Technical/Scientific Publication, 56(10), 567–572, Oct. 1974.

Primary Examiner—Douglas J. McGinty
Attorney, Agent, or Firm—Martin Barancik

[57] ABSTRACT

A foaming emulsion liquid composition comprising a. an aqueous phase comprising (1) at least one high foaming anionic surfactant and (2) at least one a mild to the skin foaming surfactant selected from the group consisting of an anionic surfactant, amphoteric surfactant nonionic surfactant, or mixture thereof wherein (a) the weight ratio of a (1) to a (2) when an a (2) anionic surfactant is present is from about 10:1 to 2:1, (b) the amphoteric is present from 0 to 10 wt % of the composition, provided that if a nonionic a (2) surfactant is not present, the amphoteric surfactant is at least 1 wt % of the composition, (c) the foaming nonionic surfactant is present from 0 to 5 wt % of the composition provided that if an amphoteric a (2) surfactant is not present the foaming nonionic surfactant is at least 1 wt % of the composition, and (d) the total a surfactant is from about 12 to 30 wt % of the composition, b. an oil phase essentially insoluble in the aqueous phase present in about 3 to 15 wt % of the composition, b. an emulsification system which provides physical stability to the formed emulsion, and comprises (1) an oil soluble, water dispersible component and (2) a water soluble, oil dispersible component.

8 Claims, No Drawings

FOAMING OIL-IN-WATER EMULSION

This is a continuation of application Ser. No. 08/170,575 filed Dec. 20, 1993 now U.S. Pat. No. 5,518,647.

BACKGROUND OF THE INVENTION

Foaming emulsions, particularly for shower gel products, are becoming increasingly popular in various areas of the world. These compositions can provide skin cleansing and caring in one application. Other applications of such compositions include facial/make-up removal "in one," baby skin cleansing and the like.

In order to have a successful product, one should have a physically stable composition with high foaming characteristics but which remains mild to the skin and provide an appropriate skin feel, conditioning effect after use. It is a difficult task to provide both physical stability of an emulsion together with the high foaming action. These two attributes plus the proper skin feel are potentially achievable in a single composition.

The composition of this invention provides such attributes and preferably provides a minimum threshold of foam according to a specific test system.

SUMMARY OF THE INVENTION

In accordance with the invention, there is a foaming emulsion liquid composition comprising:
a. an aqueous phase comprising (1) at least one high foaming anionic surfactant and (2) at least one of a mild to the skin foaming surfactant selected from the group consisting of an anionic surfactant, amphoteric surfactant, nonionic surfactant, or mixture thereof and
  (a) the weight ratio of a (1) to an a (2) anionic surfactant if present is from about 10:1 to 2:1,
  (b) the amphoteric surfactant is present from 0 to 10wt % of the composition, provided that if a nonionic a (2) surfactant is not present, the amphoteric surfactant is at least 1 wt % of the composition,
  (c) the foaming nonionic surfactant is present from 0 to 5 wt % of the composition provided that if an amphoteric a (2) surfactant is not present the foaming nonionic surfactant is at least 1 wt % of the composition, and
  (d) the total a surfactant is from about 12 to 30 wt % of the composition,
b. an oil phase essentially insoluble in the aqueous phase present in about 3 to 15 wt % of the composition,
c. an emulsification system which provides physical stability to the formed emulsion, and comprises
  (1) an oil soluble, water dispersible component, and
  (2) a water soluble, oil dispersible component.

DETAILED DESCRIPTION OF THE INVENTION

In the composition, the aqueous phase provides at least the foaminess and cleansing portion of the formulation. Examples of high foaming anionic surfactants which can be employed include the long chain alkyl sulfates, long chain alkyl sulfonates, alkoxylated preferably ethoxylated materials thereof, soaps such as long chain alkyl carboxylates, and the like. Long chain is intended to include carbon atom chain lengths of about 8 to 20, preferably 8 to 18. Normal is preferred over branched. Although described as alkyl, a small percentage of unsaturation generally less than about 20 wt %, preferably less than about 10 wt % of the chains may also be present in the hydrocarbon portion of the molecule.

The mild foaming surfactant is selected from the group consisting of anionic, amphoteric and nonionic. Examples of mild anionic surfactants include the acyl isethionates wherein the acyl group is about 8 to 20 carbon atoms such as sodium cocoylisethionate, long chain taurates, long chain sulfosuccinates, long chain N-acylated glutamates, N-acylated peptides, ethoxylated alkyl carboxylates, alkyl glyceryl ether sulfonates with or without ethoxyl groups and the like. The sarcosinates and acylisethionates are preferred. In all these cases, the long chain has from about 8 to 20 carbon atoms and is defined in the same manner as in the above paragraph. When the mild anionic surfactant is present the weight ratio of a (1) high foaming anionic surfactant to a (2) mild anionic surfactant is about 10:1 to 2:1, preferably 6:1 to 3:1.

The amphoteric surfactant is exemplified by the long chain glycinates, propdonates, betaines, and sulfobetaines. By long chain is meant chains as defined in the above paragraphs.

Preferred are the betaines, particularly the long chain amido alkyl betaines of about 8 to 20 carbon atoms such as cocoamidopropylbetaine. The amphoteric material is present from about 0 to 10 wt % of the composition, preferably 2 to 5 wt %. If no nonionic surfactant is present, then at least 1 wt % of the amphoteric surfactant must be present.

Examples of foaming nonionic water soluble surfactants include alkanolamides, amine oxides and the alkylpolysaccharides. Examples of alkanolamides include monoethanolamide and coconut diethanolamide. Examples of N-oxides include long chain alkyldimethylaminoxide and ethoxylated derivatives thereof. Examples of the saccharides include oligomers and polymers, preferably oligomers of glucose, fructose, mannose, and the like. Alkyl chain lengths of about 8 to 16 carbon atoms can be employed. An average degree of polymerization of the saccharide units of about 1.2 to 2 is preferred. Decyl or lauryl polyglucose are preferred alkylpolysaccharides. These foaming nonionic surfactants can be obtained under trademarks Oramix NS10, NS26 and NS 06 from SEPPIC and Plantaren 1200 and 2000 from Henkel. These surfactants are present in the composition at levels of 0 to 5 wt % of the composition preferably about 1 to 4 wt %. If an amphoteric surfactant is absent from the composition, then at least 1 wt % of a foaming nonionic surfactant must be present in the composition.

The total amount of foaming surfactant "a" is from about 12 to 30 wt % of the composition preferably about 15 to 27 wt %.

The oil phase of the composition is essentially responsible for providing the emulsion and the skin conditioning, feel, to the composition. The oil phase is essentially insoluble but dispersible within the aqueous phase. The oil phase comprises materials such as and including vegetable oils, mineral oils, petrolatrums, silicones and the like. Examples of vegetable oils includes jojoba, wheat germ, soya, sunflower, castor, corn, safflower, sesame, corn germs, apricot kernels, palm kernel, palm, olive, meadowfoam seed, macadamia nut, avocado and, mixtures thereof. Mineral oils (paraffiin oil) are a liquid mixture of hydrocarbons derived from petroleum. Petrolatums are a general description for a semi solid mixture of hydrocarbons derived from petroleum. Examples of silicones include dimethicone, methylphenyl siloxanes and their derivatives. The oil phase should be present in the composition in about 3 to 15 wt %, preferably about 5 to 12 wt %.

The third component the composition is "c", an emulsification system which provides physical stability to the formed emulsion. This emulsification system is comprised of (1) a water dispersible oil soluble component and (2) a water soluble oil dispersable component. It is important to maintain a proper balance between the lipophilicity and hydrophilicity of the composition. In this type of composition it is very important to maintain the emulsion as measured by viscosity profile, and visual assessment of homogeneity through a significant time period since emulsions have a tendency to separate or fall apart. Users of this type of product have the expectations of obtaining from the container a homogeneous creamy/milky product. A further preferred advantage is that the emulsification system should have the ability to accomplish its goal(s) without having a significant negative effect on foam performance, that is foaming should not be compromised.

The physical stabilization arising from the emulsification system (1) oil soluble component is brought about by using long chain ethoxylated alcohols or cyclic alcohols (sugars), preferably alkylated or acylated with a long chain alkyl group of 8 to 24 carbon atoms together with a free fatty acid. By long chain with reference to the alcohol is meant alkyl or alkenyl of 6 to 18, preferably 8 to 14 carbon atoms, not counting the alkoxy carbons which is alkoxylated (ethoxylated and/or propoxylated, with 2 to 15 groups, preferably ethoxylated). Examples of such alcohols include oleth-5 available as Emulsogen LP from Hoechst (average of 5 ethoxy groups) and a $C_{16}$–$C_{18}$ five ethoxylated fatty alcohol obtained as Nacolox 1618-50 from Condea. The cyclic alcohols are preferably 5 or 6 carbon atoms. However lesser alcohol substituted cycloalkylene moieties of 5 to 7 carbon atoms can also be employed such as sorbitan laurate available as Span 20 from ICI. These materials can also be alkoxylated preferably ethoxylated. The sugars preferably have alkyl groups attached thereto in some manner such as through an ether or ester bond. The length of the alkyl group is not unduly significant and can be from about 8 to 20 carbon atoms, preferably 10 to 20. Examples of such effective emulsifying materials in this system include cetearyl glucoside available as Montanov 68 from Seppic sometimes employed in combination with a hydrophilic nonionic co-emulsifier of HLB at least equal to 9.5 like polysorbate 60 or ceteth 20. Further examples include sucroglycerides such as Mirasoft MSP 011 a palm oil acylated sucrose from Rhone Poulenc and an ester of an alkyl glucoside such as polyglyceryl methylglucose distearate (Tego Care 450 from Goldschmidt) present alone or in combination with a small amount of glycerylmonostearate. The Mircrosoft from Rhone Poulenc are generally complex mixtures of sucrose ester and glycerides resulting from the transestearification a natural triglyceride such as coconut oil or palm oil with sucrose. In each of the specifically named and identified systems above, the composition physical stability is maintained without significantly compromising foam performance as measured by the modified Ross and Miles ISO 696 test described later. The alkylated or acylated sugar material acting as emulsifiying agents are generally monosaccharide such as glucose but can be oligomeric in nature up to an average degree of polymerization of 3 preferably 2. Sucrose, a combination of two different sugars is an example of such a material. They are essentially nonfoaming in nature in contrast to the nonionic foaming agents of "a". Other potentially active emulsification systems such as glyceryl stearate and PEG-100 stearate do provide physically stable emulsions but dramatically impair foam performance as measured by the above noted method.

Quantities of these emulsification oil soluble, water dispersible alcoholic type materials should be from about 1 to about 10wt % of the composition, preferably about 2 to 6wt %.

The second essential portion of the oil soluble, water dispersible component of the emulsion system is a free fatty carboxylic acid having from about 8 to 20 carbon atoms, inclusive, preferably 10 to 18 carbon atoms. The acyl groupings are generally saturated but can have up to 20 wt %, preferably up to 10 wt % alkenyl grouping. The hydrocarbon groups are preferably normal than branched but a small amount of branching or branched groups can be present. The preferred fatty acid is lauric. Both emulsion stability activity and lack of negative impact on foam performance are present when the fatty acids are employed. The quantity of free fatty acid in the composition is from about 0.5 to 8 wt %, preferably about 2 to 5 wt %.

The second component of the emulsion system is a water soluble, oil dispersible material which provides further stability to the emulsion. Preferred are water soluble polymer systems based on guar gum. Alkoxylated guar such as hydroxy propyl guar are particularly preferred. Quaternized derivatives of guars, especially hydroxy propyl guar are particularly preferred. Jaguar C-162 from Rhone Poulenc, the hydroxy propyl trimonium chloride derivative of hydroxy propyl guar is particularly effective since it provides increased skin feel as well as emulsion stability to the composition. About 0.01 to 4 wt %, preferably about 0.02 to 1 wt % of the composition is effective.

Additionally it has been found that the presence of small amounts of a water soluble polymer system provides additional emulsion stability and/or skin feel to the composition. Examples of such polymer system include cellulosic polymer preferably alkoxylated and also quaternized, proteins and their dervatives, preferably quaternized; vinylic polymers quaternized or not; acrylates, acrylate/alkylacrylate copolymers and polyacrylamides. The acrylate acylamide type systems are available as Carbopol from Goodrich and Sepigel from Seppic. All polymers under the general CTFA name "polyquaternium" can also be employed. The preferred additinal polymer system is the cellulosic based, preferably alkyl dimonium hydroxyethyl cellulose available as Crodacel QS from CRODA. These quaternized polyethers provide both skin feel and additional stabilization to the emulsion. Moreover the quaternized cellulose (Crodacel QS) provides significant foam stabilization and foam boosting in the composition as measured by a modified Ross-Miles method. The quantities of these additional polymer systems present in the composition are relatively low—about 0 to 2 wt % of the composition, preferably about 0.02 to 1 wt %.

Depending upon the amount of skin feel which is desired, other materials which promote the skin feel but preferably not adversely affect the foam can also be present. These materials are nonionic, generally nonfoaming ethoxylated glycerides organic alcohols or long-chain carboxylic acid esters where the ester grouping is preferably the glyceryl ester of a long chain carboxylic acid such as coco acid, stearic acid, palmitic acid and the like. Examples of these materials include PPG-5 laureth-5, PEG-7 glyceryl cocoate, glyceryl laurate, and PEG-45 Palm Kernel Glycerides. Quantities of these surfactants are from about 0 to 10 wt % of the composition, preferably about 2 to 8 wt %.

These compositions have both excellent cleansing abilities and skin feel attributes. The emulsion is particularly stable and provides excellent foam. In fact, these compositions preferably provide foaming at or above 450ml on the Ross & Miles modified method. The Ross-Miles method as described as ISO 696-1975E is followed as the test procedure except for the following modification.

The modification involves generating foam by a useage condition which approximates that of a shower gel, that is a high mechanical energy. The cyclinder with the sample composition is rotated by means of an electric motor and present in the cylinder a plastic agitator of dimensions height 7.2 in and radium 1.2 cm and weight 18.5 grams +0.5 grams. The experimental procedure followed in the experimentation is adding 2.5 grams of test product to 97.5 grams water of 250 ppm hardness at 41° C. This sample–then poured into a 500 ml calibrated cylinder containing the above described plastic agitator. The cylinder capped and agitated electrically at a rate of five revolutions per 10 seconds. Milliliters of foam are noted as a function of time or revolutions and are plotted against the other. Such graphical data is a measure of foam speed/quickness. Once maximum foam height is reached, a plateau, rotation is stopped. The cylinder is allowed to rest and foam height is measured again after ten (10) minutes. The percentage of maximum foam height lost after this ten (10) minute period is an indication of the foam stability. Utilizing this test system, certain composition formulations can deliver a better foam profile than two commercial aqueous foaming emulsion systems currently on sale in Europe.

Other materials can also be present in the composition such as preservatives, emollients, humectants (glycerine), chelating agents UV stabilizers, antibacterials, dyes, fragrances and the like. Generally the remainder of the composition is water.

Below are examples of the invention. These examples are intended to illustrate the broad concept of the invention and are not intended to limit such concept.

In the examples SLES is sodium laureth-2-sulfate. The vegetable oil are equal quantities of sesame seed, safflower seed and wheat germ oil. A small amount of glycerine is also present in each of the compositions for purposes of humectant activity. 0.2 wt % crodacel QS from Croda, previously identified, is also present in all the examples. The decylpolyglucose used in the examples is Cramix NS10 from Seppic.

| | Wt % |
|---|---|
| Example 1 | |
| SLES | 12% |
| Cocamidopropyl betaine | 3% |
| Decylpolyglucose | 3% |
| Lauric acid | 4% |
| Sodium cocoyl isethionate | 4% |
| Oleth-5 | 5% |
| Hydroxyl propyl guar hydroxypropyl trimonium chloride | 0.5% |
| Vegetable oils mixture | 6% |
| Example 2 | |
| SLES | 12% |
| Cocamidopropyl betaine | 3% |
| Decylpolyglucose | 3% |
| Lauric acid | 4% |
| Sodium lauryl sarcosinate | 2% |
| Oleth-5 | 5% |
| Hydroxyl propyl guar hydroxypropyl trimonium chloride | 0.5% |
| Vegetable oils mixture | 6% |
| Example 3 | |
| SLES | 12% |
| Cocamidopropyl betaine | 3% |
| Decylpolyglucose | 3% |
| Lauric acid | 4% |
| Sodium lauryl sarcosinate | 2% |
| Cetearyl glucoside | 2% |
| Polysorbate 60 | 1.25% |
| Hydroxyl propyl guar hydroxypropyl trimonium chloride | 0.5% |
| Vegetable oils mixture | 6% |

-continued

| | Wt % |
|---|---|
| Example 4 | |
| SLES | 12% |
| Cocamidopropyl betaine | 3% |
| Decylpolyglucose | 3% |
| Lauric acid | 4% |
| Sodium lauryl sarcosinate | 2% |
| Polyglyceryl methyl glucose distearate | 3% |
| Glyceryl monostearate | 1% |
| Hydroxyl propyl guar hydroxypropyl trimonium chloride | 0.5% |
| Vegetable oils mixture | 6% |
| Example 5 | |
| SLES | 12% |
| Cocamidopropyl betaine | 3% |
| Decylpolyglucose | 3% |
| Lauric acid | 4% |
| Sodium lauryl sarcosinate | 2% |
| Methyl glucose dioleate | 2% |
| PEG-20 methyl glucose distearate | 3% |
| Hydroxyl propyl guar hydroxypropyl trimonium chloride | 0.5% |
| Vegetable oils mixture | 6% |
| Example 6 | |
| SLES | 12% |
| Cocamidopropyl betaine | 3% |
| Decylpolyglucose | 3% |
| Lauric acid | 4% |
| Sodium lauryl sarcosinate | 2% |
| Mirasoft MSP 011 from Rhone-Poulenc (Palm Oil Sucroglyreride) | 2.5% |
| Hydroxyl propyl guar hydroxypropyl trimonium chloride | 0.5% |
| Vegetable oils mixture | 6% |

In limited sensory testing to date, Examples 4 and 6 provided better foam quality and feel as well as better skin feel on dry skin than "Litamin 2 in 1", a commercial foaming emulsion product in the same target area. The examples using oleth-5 (Emulsogen) appear to be at least equivalent to Litamin 2 in 1 in terms of foam and skin feel. In in vitro testing using the modified Ross Miles method previously described, Examples 2,3,4 and 6 performed better than Litamin 2 in 1 and gave at least 450 mls. of foam.

I claim:

1. A foaming oil in water emulsion liquid composition comprising a. an aqueous phase comprising (1) at least one high foaming anionic surfactant and (2) at least one mild to the skin foaming surfactant selected from the group consisting of an anionic surfactant, amphoteric surfactant, nonionic surfactant, or mixture thereof wherein (a) the weight ratio of a (1) to a (2) when an a (2) anionic surfactant is present is from about 10:1 to 2:1, (b) the amphoteric is present from 0 to 10 wt. % of the composition, provided that if a nonionic a (2) surfactant is not present, the amphoteric surfactant is at least 1 wt. % of the composition, (c) the nonionic surfactant is present from 0 to 5 wt. % of the composition provided that if an amphoteric a (2) surfactant is not present, the foaming nonionic surfactant is at least 1 wt. % of the composition, and (d) the total of surfactants is from about 12 to 30 wt. % of the composition, b. an oil phase essentially insoluble in the aqueous phase present in about 3 to 15 wt. % of the composition.

c. an emulsification system which provides physical stability to the formed emulsion which comprises c(1) an oil soluble water dispersible component comprising a free fatty acid and an essentially non-foaming material selected from the group consisting of a long chain alkyl or alkenyl alcohol having 2 to 15 alkoxy groups, a 5 or 6 carbon atom cycloalkylene ring system having at least one hydroxy group and substituted with at least one long chain alkyl, alkenyl or alkoxylated alkyl or alkenyl group or a long chain acyl group optionally alkoxylated whereby an etheric or a carboxy ester bond is formed with the hydroxy of the cycloalkylene ring system, a sugar with an average degree of polymerization of 1 to 2 and substituted with at least one long chain alkyl, alkenyl or alkoxylated alkyl or alkenyl group or a long chain acyl group optionally alkoxylated whereby an etheric or a carboxy ester bond is formed with the hydroxy of the cycloalkylene ring system wherein said material is from about 1 to about 10 wt. % of the composition and c(2) a guar and a quaternized cellulosic polymer in emulsion stabilizing and skin feel quantities, the total amount of c(1) and c(2) being from about 1.53 to about 23 wt. % of the composition.

2. The composition in accordance with claim 1 wherein the c material comprises at least one selected from the group consisting of oleth-5; cetearyl glucose combination with a HEB>or equal to 9.5 nonionic surfactant; sucroglyceride; ester of methylglucoside optionally in combination with a glyoeryl ester of a long chain carboxy acid; a sorbitan ester of a long chain carboxy acid; and mixtures thereof.

3. The composition in accordance with claim 1 wherein c(1) comprises a long-chain alkyl or alkenyl alcohol having 2 to 15 alkoxy groups.

4. The composition in accordance with claim 1 wherein c(1) comprises a 5 or 6 carbon atom cycloakylene ring system having at least one hydroxy group and substituted with at least one long-chain alkyl, alkenyl or alkoxylated alkyl or alkenyl group or a long-chain acyl group optionally alkoxylated whereby an etheric or a carboxy ester bond is formed with the hydroxy of the cycloalkylene ting system.

5. The composition in accordance with claim 1 wherein c(1) comprises a sugar with an average degree of polymerization of 1 to 2 and substituted with at least one long-chain alkyl, alkenyl or an alkoxylated alkyl or alkenyl group or a long-chain acyl group optionally alkoxylated whereby an etheric or a carboxy ester bond is formed with the hydroxy of the cycloalkylene ring system.

6. The composition in accordance with claim 1 wherein c(1) comprises a sucroglyceride.

7. The composition in accordance with claim 1 wherein c(1) comprises oleth-5.

8. The composition in accordance with claim 1 wherein c(1) comprises cetearyl glucoside.

* * * * *